(12) United States Patent
Rasche et al.

(10) Patent No.: US 6,865,248 B1
(45) Date of Patent: Mar. 8, 2005

(54) METHOD AND DEVICE FOR ACQUIRING A THREE-DIMENSIONAL IMAGE DATA SET OF A MOVING ORGAN OF THE BODY

(75) Inventors: Volker Rasche, Hamburg (DE); Michael Grass, Hamburg (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/668,938

(22) Filed: Sep. 25, 2000

(30) Foreign Application Priority Data

Sep. 25, 1999 (DE) ......................................... 199 46 092

(51) Int. Cl.$^7$ ............................................. G01N 23/00
(52) U.S. Cl. ............................................. 378/8; 378/4
(58) Field of Search ........................................ 378/98, 8

(56) References Cited

U.S. PATENT DOCUMENTS

| | | | | |
|---|---|---|---|---|
| 3,871,360 A | * | 3/1975 | Van Horn et al. | 600/484 |
| 4,075,489 A | * | 2/1978 | Neal et al. | 378/10 |
| 5,383,231 A | | 1/1995 | Yamagishi | 378/15 |
| 5,482,042 A | * | 1/1996 | Fujita | 600/428 |
| 5,751,782 A | * | 5/1998 | Yoshitome | 378/98.5 |
| 6,470,066 B2 | * | 10/2002 | Takagi et al. | 378/8 |

* cited by examiner

Primary Examiner—Edward J. Glick
(74) Attorney, Agent, or Firm—John Vodopia

(57) ABSTRACT

The invention relates to a method of and a device for the formation of a three-dimensional image data set of a periodically moving body organ (11) of a patient (5) by means of an X-ray device (1) which includes an X-ray source and an X-ray detector (3), a motion signal (H, B) which is related to the periodic motion of the body organ (11) being measured simultaneously with the acquisition of the projection data sets ($D_0$, $D_1$, ..., $D_{16}$). In order to improve such a method or such a device, notably in order to improve the construction and to reduce the time required for data processing while keeping the radiation dose for the patient as small as possible and while ensuring an as high as possible image quality, the invention proposes to acquire the projection data sets ($D_0$, $D_1$, ..., $D_{16}$) necessary for the formation of the three-dimensional image data set successively from different X-ray positions ($p_0$, $p_1$, ..., $p_{16}$) which are situated in one plane, to control the X-ray device by means of the motion signal (H, B) in such a manner that a projection data set ($D_0$, $D_1$, ..., $D_{16}$) is acquired during a low-motion phase of the body organ (11) in each X-ray position ($p_0$, $p_1$, $p_{16}$) required for the formation of the three-dimensional image data set, and to use the projection data sets ($D_0$, $D_1$, ..., $D_{16}$) acquired during the low-motion phase for the formation of the three-dimensional image data set.

16 Claims, 3 Drawing Sheets

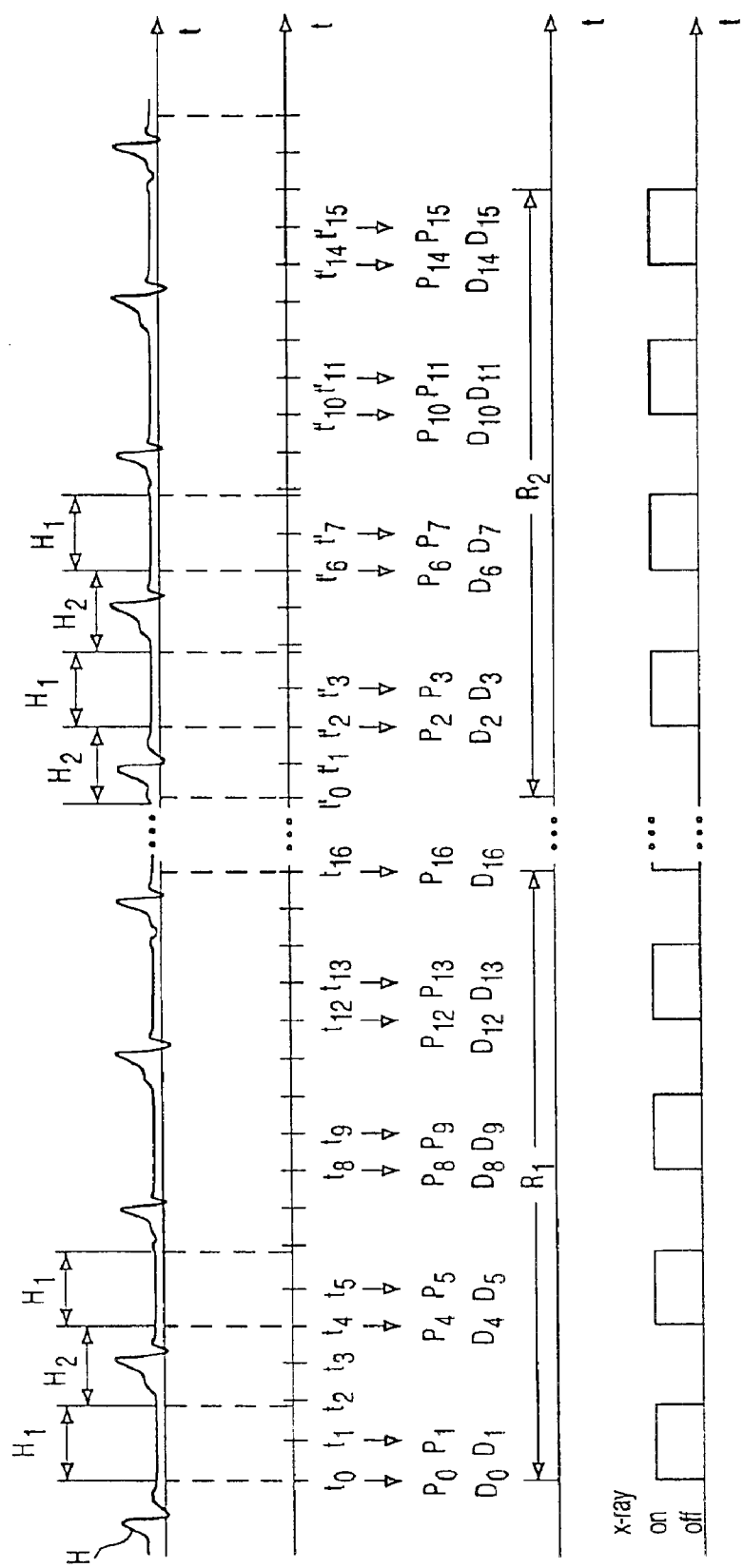

METHOD AND DEVICE FOR ACQUIRING A THREE-DIMENSIONAL IMAGE DATA SET OF A MOVING ORGAN OF THE BODY

BACKGROUND OF THE INVENTION

The invention relates to a method of acquiring a three-dimensional image data set of a periodically moving organ of the body of a patient by means of an X-ray device in which projection data sets are acquired by the X-ray device simultaneously with a motion signal related to the periodic motion of the organ. The present invention also relates to an X-ray device including an X-ray source and an X-ray detector for acquiring projection data sets from different X-ray positions and enabling the formation of a three-dimensional image data set of a moving organ of the body of a patient from the projection data sets, and a mechanism for measuring a motion signal related to the periodic motion of the organ which is acquired simultaneously with the acquisition of projection data sets.

SUMMARY OF THE INVENTION

For the acquisition of a three-dimensional image data set of an object by means of an X-ray device it is necessary to acquire a plurality of sets of projection data from different X-ray positions and to calculate therefrom, while using a suitable reconstruction algorithm, the three-dimensional image data set wherefrom a desired image of the object can be formed. The quality of such an image is dependent notably on how many projection data sets are acquired, that is, on the number of different X-ray positions wherefrom acquisition takes place, on the level of the contrast between the object to be imaged and its environment, as well as on the amount of motion of the object during the acquisition of the sets of projection data. All of said factors could give rise to disturbing artifacts in the image to be formed.

The problem of inadequate contrast can be solved, for example by means of a contrast medium. For example, when images of the coronary vessels are to be formed, a contrast medium can be injected therein by means of a catheter; this medium remains in the coronary vessels for approximately 4 seconds, so that in the projection data sets acquired during this period of time these vessels exhibit a high contrast relative to their environment. However, at present it is not possible to acquire during this period of time all the sets of projection data necessary for the acquisition of a three-dimensional image data set, so that it is necessary to inject contrast medium a number of times in succession and to acquire projection data sets successively during a plurality of X-ray cycles. However, a further problem is then encountered in that the heart pulsates continuously, that is, that it performs an eigenmotion, and that, moreover, the heart is moved to and fro due to the respiratory motion of the patient. Other organs of interest in the body, for example the liver or the brain, also move periodically, notably because of the pulsating motion of the heart and the respiratory motion of the patient. Consequently, the projection data sets acquired contain information on the relevant organ of the body examined in different phases of motion, so that a three-dimensional image data set determined from such projection data sets contains artifacts.

U.S. Pat. No. 5,383,231 discloses a computed tomography (CT) system in which the projection data sets are acquired during a helical scanning motion of the X-ray source and the X-ray detector about the patient. At the same time, and independently therefrom, an electrocardiogram of the patient is recorded, the data of said electrocardiogram being used during the formation of the CT images and a three-dimensional image data set from the projection data sets so as to take into account the displacement of the patient table during the acquisition of the projection data sets and to evaluate exclusively the projection data sets acquired during a given phase of the cardiac motion. In order to realize a three-dimensional image data set therein, however, it is first necessary to calculate CT image data sets from the projection data sets; a three-dimensional image data set can then be formed from the three-dimensional image set by means of interpolation algorithms. Furthermore, no direct and immediate link is provided between the acquisition of the electrocardiogram and the acquisition of the projection data sets by means of the X-ray device, so that a series of projection data sets which have been acquired during the wrong cardiac motion phase are not evaluated.

It is an object of the present invention to improve the described method and the described X-ray device, notably to simplify the construction of such an X-ray device and to enable the data processing within a shorter period of time while exposing the patient to an as small as possible radiation dose, and to achieve an as high as possible image quality.

This object is achieved by means of a method and an X-ray device in which simultaneously with detection of the motion signal, the X-ray device is moved to different X-ray positions situated in a common plane and a projection data set is acquired when the X-ray device is in each X-ray position. The movement of the X-ray device and acquisition of the projection data sets by the X-ray device are controlled by means of the motion signal such that a projection data set during a low-motion phase of the organ is acquired when the X-ray device is in each X-ray position. The projection data sets acquired during the low-motion phases are used for the formation of the three-dimensional image data set.

Granted, it is in principle possible to reduce the number of X-ray positions and the number of projection data sets to be acquired and to replace individual projection data sets by interpolated data. However, this always degrades the image quality and such a reduction of the acquired data can be continued to a given lower limit only; below this limit various effects during the data processing, for example the effect of superposition which is due to an insufficient sampling rate, make the formation of a three-dimensional image data set hardly possible or even impossible. Therefore, in accordance with the invention a projection data set of the body organ to be examined is acquired in each X-ray position necessary for the acquisition of a three-dimensional image data set, that is, each time during a low-motion phase of the periodically moving body organ. The periodically moving body organ may at the same time be the body organ to be examined or a body organ which induces a likewise periodic motion of the body organ to be examined (for example, the body organ to be examined may be the brain whose periodic motion is linked to the periodic motion of the heart in such a manner that the brain performs a motion with the same period as the heart). The motion signal acquired at the same time is used to control the X-ray device and the data acquisition according to the invention. The acquisition of the projection data sets need not take place in the sequence of the successively occupied X-ray positions; it is also possible to occupy individual X-ray positions, or all X-ray positions, several times, each time a respective projection data set being acquired and it merely being necessary to ensure that at least one projection data set is acquired during a low-motion phase in each X-ray position.

Various attractive versions of the method according to the invention and various attractive embodiments of the X-ray device according to the invention are disclosed below.

It is particularly advantageous to use versions in which a respiratory motion signal which is dependent on the respiration of the patient and/or a cardiac motion signal which is dependent on the motion of the heart, notably an electrocardiogram, are acquired. The choice as to which of these signals is acquired and used for the control of the X-ray device and the data acquisition is dependent notably on what influences the motion of the body organ to be examined. For example, when the heart is considered, we find that it performs a rotational as well as a translational motion. In the systolic phase, in which the ventricles contract and discharge the blood from the heart, the motion is more pronounced than in the diastolic phase in which the ventricles are slowly filled with blood again and the heart expands. On this eigenmotion of the heart there is superposed the respiratory motion, because the heart is shifted towards the head of the patient and is tilted slightly towards the back during inhalation, whereas it returns to the original position during exhalation.

Therefore, in further versions of the invention there is also acquired a respiratory motion signal which is dependent on the respiratory motion of the patient and on the basis thereof projection data sets are selected so as to determine the three-dimensional image data set, all of such projection data sets having been acquired during the same respiratory motion phase, for example in the state of exhalation. The respiratory motion signal can also be used to process projection data sets which have been acquired in different respiratory motion phases so as to form the three-dimensional image data set, the position shifts of the body organ to be examined then being corrected for on the basis of the respiratory motion. This implies, for example, that the motion or the position of the body organ is known in each respiratory motion phase or that it can be assumed to be a model.

In a further version of the invention the respiratory motion signal can be used to inform the patient that a desired respiratory motion phase has been reached, for example, the state of exhalation, so that the patient can hold his or her breath for as long as possible during this phase of respiratory motion and as many projection data sets as possible can be acquired from different X-ray positions during this time.

A cardiac motion signal as acquired in versions of the invention can be used to acquire the projection data sets for the formation of the three-dimensional image data sets exclusively during the diastolic phase of the cardiac motion in which the motion of the heart is significantly less than in the systolic phase, or to acquire projection data sets exclusively when the heart is exactly in the diastolic phase. Projection data sets acquired in the systolic phase are then either not used further or even are not acquired at all; the X-ray device can be controlled accordingly for this purpose.

Advantageous embodiments of the means for measuring the motion signal are disclosed below.

BRIEF DESCRIPTION OF THE DRAWINGS

The invention will be described in detail hereinafter with reference to the drawings. Therein:

FIG. 4 shows a further time diagram of a cardiac motion signal in order to illustrate a further version of the method according to the invention.

DESCRIPTION OF THE PREFERRED EMBODIMENTS

Figure 1:
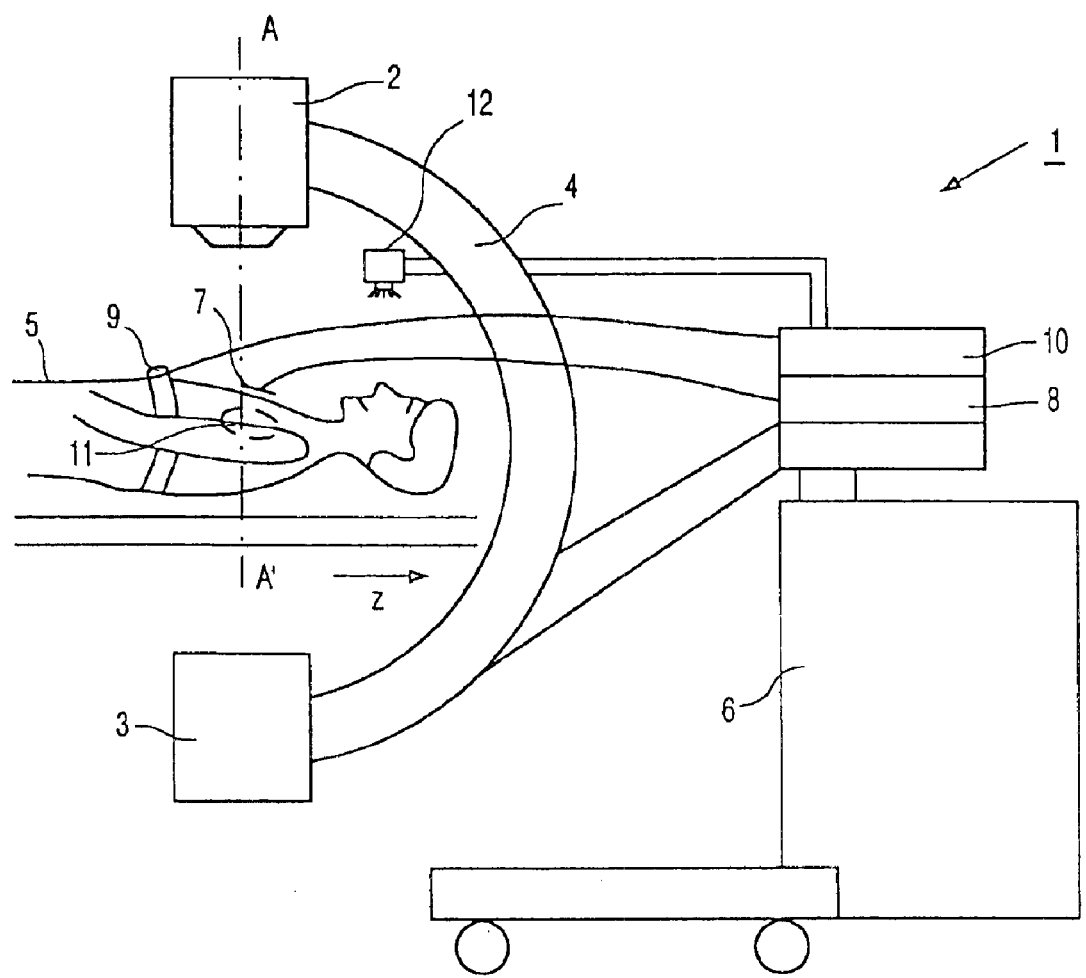
FIG. 1 shows an X-ray device according to the invention.

The X-ray device 1 shown in FIG. 1 includes an X-ray tube 2 and a two-dimensional X-ray detector 3, for example an image intensifier, which are mounted on a C-arm 4 in such a manner that they are arranged so as to be rotatable about the z axis and around a patient 5 and can be tilted about an axis extending perpendicularly thereto. The X-ray device 1 and the processing of the data acquired by means of the X-ray detector 3 are controlled by the control and arithmetic unit 6. Electrodes 7 which are connected to an electrocardiography device 8 are arranged on the chest of a patient 5 in order to record an electrocardiogram of the patient. The respiratory motion of the patient 5 is measured by means of an abdominal belt 9 which can be distorted by the respiratory motion and is connected to a respiratory motion measuring device 10 in order to form a respiratory motion signal. The electrocardiogram and the respiratory motion signal are conducted on-line to the control and arithmetic unit 6 by the electrocardiography device 8 and the respiratory motion measuring device 10, respectively, in order to be taken into account directly during the control of the X-ray device 1 and the data acquisition.

In the case shown the X-ray device 1 occupies an X-ray position for the acquisition of a projection data set of the heart 11. In order to enable acquisition, during the same respiratory motion phase, of all projection data sets required for the formation of a three-dimensional image data set, the embodiment shown is provided with a signal device 12 which informs the patient 5 that a desired respiratory motion phase has been reached, that is, for example, the state of exhalation, so that the patient can hold his or her breath for as long as possible. During this period projection data sets of the heart 11 can be acquired from different X-ray positions, without a motion due to the respiratory motion of the patient 5 being superposed on the eigenmotion of the heart 11.

Figure 2:
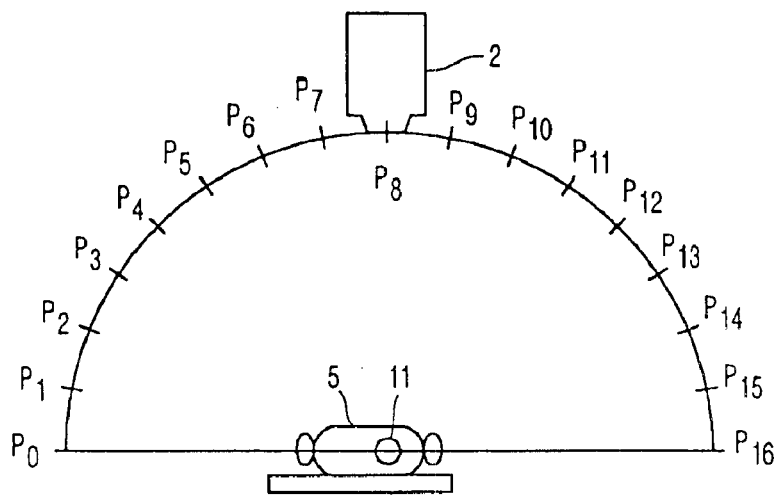
FIG. 2 illustrates different X-ray positions during an X-ray cycle.

FIG. 2 is a sectional view taken along the line A-A'. This Figure shows symbolically the X-ray positions $p_0$ to $p_{16}$ which are situated on a semicircular arc and are successively occupied by the X-ray tube 2 so as to acquire a respective projection data set. In order to obtain a three-dimensional image data set wherefrom desired representations of the heart can be formed, for example, individual slice images or images of the coronary vessels, it is necessary to acquire a respective projection data set in each of the X-ray positions $p_0$ to $p_{16}$ shown, the number of X-ray positions shown being chosen so as to be small for the sake of simplicity.

Figure 3:
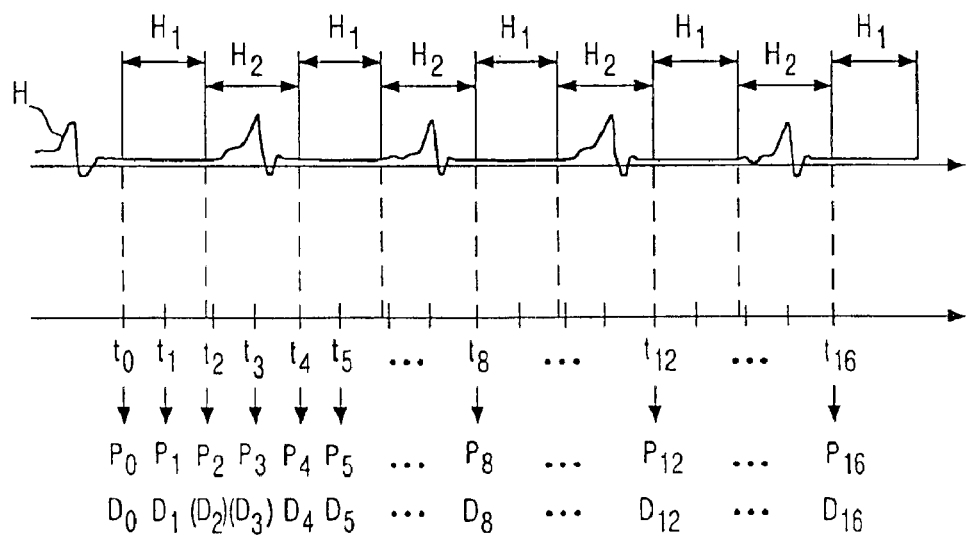
FIG. 3 shows a time diagram of a cardiac motion signal in order to illustrate the acquisition of the projection data sets according to the invention.

In order to take into account the fact that the heart 11 performs an eigenmotion during the acquisition of the projection data sets, in one embodiment of the invention an electrocardiogram H as shown in FIG. 3 is measured as a motion signal simultaneously with the acquisition of the projection data sets. The individual instants $t_0, t_1, \ldots, t_{16}$ are marked on a time base which is shown underneath the electrocardiogram H; the X-ray tube is situated in the X-ray positions $p_0, p_1, \ldots, p_{16}$ at these instants at which a respective projection data set $D_0, D_1, \ldots, D_{16}$ is acquired. As is clearly shown in FIG. 3, each time two projection data sets ($D_0, D_1; D_4, D_5; \ldots$) have been acquired during the low-motion phase $H_1$ (diastolic phase) whereas each time two other projection data sets ($D_2$, $D_3$; $D_6$, $D_7$; ...) have been acquired during a high-motion phase $H_2$ (systolic phase). In order to ensure high quality, artifact-free images of the heart, the projection data sets ($D_2$, $D_3$, $D_6$, $D_7$, ...), acquired during the high-motion phases $H_2$ cannot be used for the acquisition of the three-dimensional image data set. The remaining, usable projection data sets ($D_0$, $D_1$, $D_4$, $D_5$, ...), however, are not sufficient for the reconstruction of a three-dimensional data set of adequate quality. Therefore, all X-ray positions $p_0$ to $p_{16}$ are successively occupied a number of times during respective X-ray cycles, each X-ray cycle commencing at a different instant within a cardiac cycle as will be explained with reference to FIG. 4.

During a first X-ray cycle $R_1$ (see third time base in FIG. 4) first the X-ray positions $p_0$ to $p_{16}$ are successively occupied, only the projection data sets $D_0$, $D_1$, $D_4$, Ds, $D_{16}$ acquired during the low-motion phases $H_1$ being usable. The first X-ray cycle $R_1$ commences at the instant to at the beginning of a low-motion phase $H_1$. After a time interval, for example, necessary to move the X-ray device to the initial position again, a second X-ray cycle $R_2$ commences at an instant $t'_0$ which corresponds approximately to the beginning of a high-motion phase $H_2$. In the X-ray position $p_2$ at the instant $t'_2$ the X-ray tube is in a low-motion phase $H_1$ again, so that the projection data set $D_2$ acquired at this instant (either not acquired during the first X-ray cycle $R_1$ or not usable if it was acquired) can be used so as to form the three-dimensional image data set. The same holds for the further projection data sets $D_3$, $D_6$, $D_7$, $D_{10}$, ..., acquired during the second X-ray cycle $R_2$; these sets are then all acquired during low-motion phases $H_1$. Such control of the start of the individual X-ray cycles ensures that a projection data set $D_0$ to $D_{16}$ which has been acquired in a low-motion phase $H_1$ in every X-ray position and is suitable to derive a three-dimensional image data set therefrom will be available after two X-ray cycles.

The acquisition of the projection data sets in the individual X-ray cycles $R_1$, $R_2$ can be performed in such a manner that a respective projection data set $D_0$ to $D_{16}$ is acquired in each of the X-ray positions $p_0$ to $p_{16}$ occupied by the X-ray source, be it that only the projection data sets acquired during the low-motion phases $H_1$($D_0$, $D_1$, $D_4$, $D_5$, ... in the first X-ray cycle; $D_2$, $D_3$, $D_6$, $D_7$, ... in the second X-ray cycle) are used. In an alternative version, however, it may also be arranged that projection data sets are acquired exclusively in low-motion phases $H_1$, all X-ray positions $p_0$ to $p_{16}$ being continuously traversed nevertheless. This means that in the first X-ray cycle, for example, the positions $p_2$ and $p_3$ are occupied by the X-ray tube in a high-motion phase $H_2$, but no projection data set is acquired therein, for example, because the X-ray tube remains switched off in these positions. It appears from the lowermost time base in FIG. 4 that in this embodiment of the invention the X-ray tube is switched on only during the low-motion phases $H_1$ and that it remains switched off in the high-motion phases $H_2$. Such switching-on and off of the X-ray tube is controlled on the basis of the electrocardiogram H. This offers the advantage that the patient is not unnecessarily exposed to X-rays during high-motion phases $H_2$.

In the version of the method according to the invention which has been described with reference to FIG. 4 all necessary projection data sets $D_0$ to $D_{16}$ can be acquired within two X-ray cycles. However, this need not necessarily be so; a larger number of X-ray cycles may also be required, depending on the ratio of the duration of the low-motion phase $H_1$ to the duration of the high-motion phase $H_2$. For example, when the low-motion phase $H_1$ is very short whereas the high-motion phase $H_2$ is very long, definitely more than two X-ray cycles will be required.

Alternatively, the X-ray device can also be controlled in such a manner that the individual X-ray positions $p_0$ to $p_{16}$ are individually occupied in succession, that in each X-ray position it is tested, on the basis of the motion signal, whether at that instant a low-motion phase is concerned, and that in the positive case a projection data set is acquired whereas in the negative case the occurrence of a low-motion phase is awaited in this X-ray position, the projection data set being acquired in this X-ray position only when such a low-motion phase has been reached. The occupation of the X-ray positions and the acquisition of the projection data can also be triggered on the basis of the motion signal in such a manner that the X-ray source is always present in a new X-ray position at a fixed instant within a given phase of motion and that at the same time a correction data set is acquired so that all projection data sets are acquired at the same instant within a phase of motion.

Figure 5:
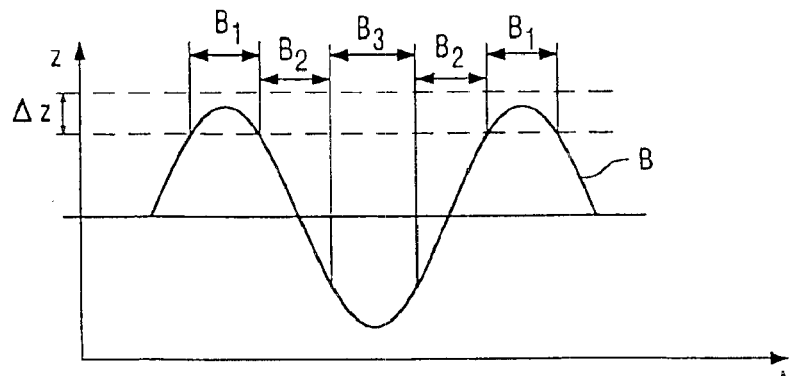
FIG. 5 shows a time diagram of a respiratory motion signal.

FIG. 5 shows a time diagram illustrating a respiratory motion signal B which has been acquired by means of an abdominal belt 9 (shown in FIG. 1) and a respiratory motion measuring device 10. This Figure shows the motion of the diaphragm of the patient 5 in the z direction. It can be seen that the motion of the diaphragm is also periodical, that in the state of exhalation $B_1$ and the state of inhalation $B_3$ rather low-motion phases are reached whereas rather high-motion phases $B_2$ occur therebetween during inhalation and exhalation. This respiratory motion signal can be used in the same way as the cardiac motion signal H described with reference to the FIGS. 3 and 4, for example, in that projection data sets are acquired exclusively during the low-motion phases $B_1$ and the X-ray device is controlled accordingly. Moreover, such a respiratory motion signal can also be acquired in addition to the cardiac motion signal in order to evaluate exclusively projection data sets which have been acquired during low-motion phases $H_1$ of the heart and also during a low-motion phase $B_1$, $B_3$ of the respiratory motion. Preferably, projection data sets are then selected which have been acquired during the same respiratory motion phase, for example, all in the state of exhalation, in order to avoid an often difficult correction (leading to inaccuracies) for the different positions of the body object to be examined in the state of inhalation and in the state of exhalation, respectively. The X-ray device can also be deliberately controlled on the basis of the respiratory motion signal and the cardiac motion signal in such a manner that individual X-ray positions are occupied in order to acquire a projection data set therein which is still missing or has been acquired in the wrong phase of motion.

Depending on the relevant application, in order to achieve adequate contrast between the body organ to be examined and its vicinity it may be necessary to administer a contrast medium to the patient briefly before the acquisition of the projection data sets. This is necessary, for example, in the case of examinations of the coronary vessels. However, because this contrast medium remains in the body organ to be examined for only a given period of time, for example approximately 4 seconds in the coronary vessels, and the duration of a single X-ray cycle is already longer (for example, from 6 to 9 seconds in the case of X-ray positions distributed through an angular range of 180° around the patient), and because a contrast medium cannot be administered arbitrarily often because of the load it represents to the patient, for such applications it is necessary to configure the method according to the invention in such a manner that the acquisition of the necessary projection data sets can take place in as short a period of time as possible. Which of the described versions is selected, however, is then dependent essentially on the applications for which the method is to be used, on the number of projection data sets required for the formation of a three-dimensional image data set for the relevant application, on the speed of acquisition of an individual projection data set or on the speed at which the individual X-ray positions can be reached, and on the ratio of the duration of a low-motion phase to the duration of a high-motion phase.

The means for measuring the cardiac motion signal and the respiratory motion signal as shown in FIG. 1 are given merely by way of example. For example, the cardiac motion signal can also be measured indirectly by means of a pulse oxymetry device whereas the measurement of the respiratory motion signal can also be performed by means of an ultrasound device or a resistance measuring device for measuring the electrical resistance of the abdominal region of the patient. Other means are also feasible in this respect. The X-ray tube and the X-ray detector may also have a different construction or be arranged in a different way. Instead of an image intensifier, a flat two-dimensional digital X-ray detector may be used and instead of a C-arm with X-ray tube and X-ray detector it is in principle also possible to use a computed tomography device configured in accordance with the invention.

What is claimed is:

1. A method for acquiring a three-dimensional image data set of a moving organ of a body of a patient, comprising the steps of:

defining a plurality of different X-ray positions of an X-ray device including an X-ray source and an X-ray detector required to obtain the three-dimensional image data set, the X-ray positions being situated in a common plane, defining an X-ray cycle in which all of the X-ray positions are successively occupied, the X-ray positions in each X-ray cycle including a common initial X-ray position and a common final X-ray position different than the initial X-ray position, detecting a motion signal related to periodic motion of the organ which has a low-motion phase and a high-motion phase, simultaneously with detection of the motion signal, successively moving the X-ray device to all of the X-ray positions in the X-ray cycle and acquiring a plurality of projection data sets required for formation of the three-dimensional image data set, each of the projection data sets being acquired when the X-ray device is in a respective one of the x-ray positions, successively completing a plurality of X-ray cycles, controlling movement of the X-ray device and the acquisition of the projection data sets by the X-ray device by means of the motion signal such that a projection data set during the low-motion phase of the organ required for the formation of the three-dimensional image data set is acquired when the X-ray device is in each X-ray position, said step of controlling the movement of the X-ray device comprising the step of controlling a start of each of the X-ray cycles based on the motion signal to cause the forthcoming X-ray cycle to commence from the initial X-ray position at a different instant in the different phases of motion of the organ than any preceding X-ray cycles, and using the projection data sets acquired during the low-motion phases for the formation of the three-dimensional image data set, said step of successively completing the plurality of X-ray cycles comprising:

beginning each X-rd-y cycle with the X-ray device in the initial X-ray position;

ending each X-ray cycle with the X-ray device in the final X-ray position; and then moving the X-ray device from the final X-ray position back to the initial X-ray position to begin a subsequent X-ray cycle in a time interval which allows the subsequent X-ray cycle to commence at a different phase of motion of the organ.

2. The method as claimed in claim 1, wherein only the projection data sets acquired during the same motion phases are selected and used.

3. The method as claimed in claim 1, wherein the X-ray device is controlled by means of the motion signal such that projection data sets are acquired only during low-motion phases of the organ.

4. The method as claimed in claim 1, wherein the X-ray device is controlled by means of the motion signal such that the X-ray source is switched on to acquire projection data sets exclusively during low-motion phases of the organ.

5. The method as claimed in claim 1, wherein a respiratory motion signal dependent on the patient's respiration is acquired as a motion signal.

6. The method as claimed in claim 5, further comprising informing the patient that a desired respiratory motion phase has been reached based on the respiratory motion signal.

7. The method as claimed in claim 1, wherein a cardiac motion signal dependent on the motion of the heart of the patient is acquired as the motion signal.

8. The method as claimed in claim 7, wherein in addition to the cardiac motion signal, a respiratory motion signal dependent on respiratory motion is acquired, further comprising using the respiratory motion signal to ensure that only projection data sets acquired during the same respiratory motion phases are used to form the three-dimensional image data set.

9. The method as claimed in claim 8, wherein the respiratory motion signal is used to correct, during the formation of the three-dimensional image data set, the projection data sets acquired in different respiratory motion phases and the shifts in position of the organ resulting therefrom.

10. The method as claimed in claim 1, further comprising the step of defining the X-ray positions on a semi-circular arc.

11. The method as claimed in claim 10, wherein the X-ray positions are set positions along the semi-circular arc.

12. The method as claimed in claim 1, wherein the organ is a heart, the start of the X-ray cycles being controlled such that each X-ray cycle commences at a different instant within a cardiac cycle.

13. The method as claimed in claim 1, further comprising the step of defining the X-ray positions on a semi-circular arc with the initial X-ray position being opposite the final X-ray position on the semi-circular arc.

14. A method for acquiring a three-dimensional image data set of a moving organ of a body of a patient, comprising the steps of:

defining a plurality of different X-ray positions of an X-ray device including an X-ray source and an X-ray detector, the X-ray positions being situated in a common plane;

detecting a motion signal related to periodic motion of the organ which has a low-motion phase;

simultaneously with detection of the motion signal, moving the X-ray device to each of the X-ray positions and when the X-ray device is in each of the X-ray positions, determining whether a low-motion phase of the organ is present by monitoring the motion signal and when a low-motion phase of the organ is present, acquiring a projection data set and when a low-motion phase of the organ is not present, maintaining the X-ray device in the X-ray position and continuously determining whether the low-motion phase is present until a positive determination is obtained and thereafter acquiring a projection data set;

continuing movement of the X-ray device to all of the X-ray positions until a projection data set is acquired when the X-ray device is in each of the X-ray positions while a low motion phase of the organ is present; and using the projection data sets acquired during the low-motion phases for formation of the three-dimensional image data set.

15. The method of claim 14, further comprising the steps of:

correlating presence of the X-ray device in each of the X-ray positions and the acquisition of the projection data sets based on the motion signal such that the X-ray device is present in a new X-ray position at a fixed instant within a given phase of motion; and then acquiring at the same time a correction data set so that all projection data sets are acquired at the same instant within a phase of motion.

16. The method of claim 14, further comprising the steps of:

defining a sequence of the X-ray positions; and moving the X-ray device successively through each of the X-ray positions in the defined sequence of X-ray positions.

* * * * *